Figure 1:
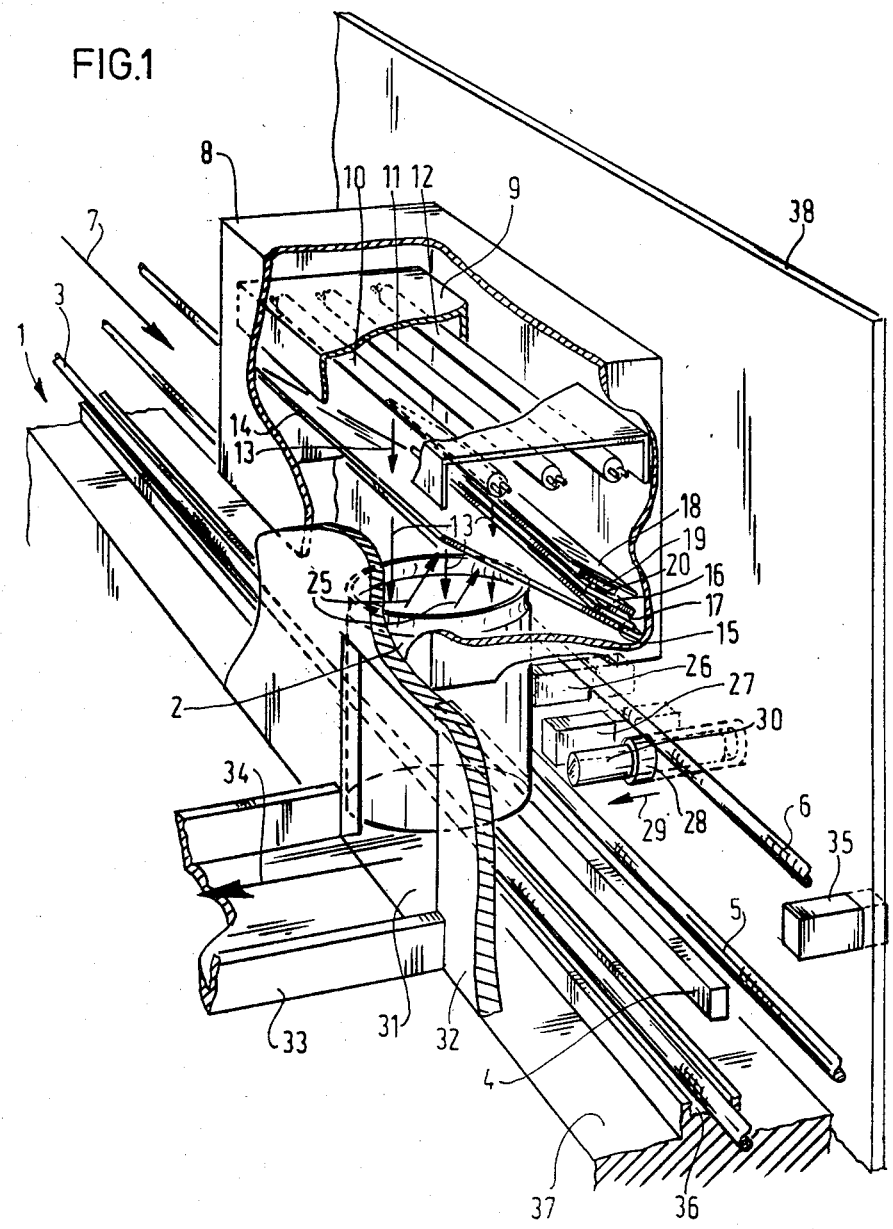

United States Patent [19]

Kleinnibbelink et al.

[11] Patent Number: 4,542,296
[45] Date of Patent: Sep. 17, 1985

[54] METHOD OF CHECKING THE COATING OF A METAL SURFACE AND DEVICE FOR CARRYING OUT THE SAME

[75] Inventors: Gerrit J. Kleinnibbelink, Apeldoorn; Anton O. Timmer, Diepenveen, both of Netherlands

[73] Assignee: Thomassen & Drijver-Verblifa N.V., Deventer, Netherlands

[21] Appl. No.: 401,320

[22] Filed: Jul. 23, 1982

[30] Foreign Application Priority Data

Jul. 23, 1981 [NL] Netherlands .......................... 8103492

[51] Int. Cl.⁴ .......................... G01J 1/42; G01N 21/90
[52] U.S. Cl. ................................. 250/359.1; 250/372; 356/237; 356/448
[58] Field of Search .................. 250/372, 359.1, 358.1, 250/360.1, 223 B, 341, 352, 504 R; 356/237, 428, 448, 446, 381; 209/577, 578, 587; 378/89

[56] References Cited

U.S. PATENT DOCUMENTS

| | | | |
|---|---|---|---|
| 2,185,690 | 1/1940 | Lane | 356/448 |
| 2,781,477 | 2/1957 | Jenner, Jr. | 250/209 |
| 3,128,879 | 4/1964 | Birchall | . |
| 3,395,278 | 7/1968 | McDivitt | 250/372 |
| 3,656,856 | 4/1972 | Katz et al. | 356/448 |
| 4,017,194 | 4/1977 | Conroy et al. | 250/223 B |
| 4,029,958 | 6/1977 | Wright | 250/223 B |
| 4,040,750 | 8/1977 | Zwiener | 356/448 |
| 4,266,878 | 5/1981 | Auer | 356/419 |

FOREIGN PATENT DOCUMENTS

| | | | |
|---|---|---|---|
| 47612 | 3/1982 | European Pat. Off. | 356/237 |
| 52-43482 | 5/1977 | Japan | . |
| 55-9170 | 1/1980 | Japan | . |
| 648552 | 1/1951 | United Kingdom | . |

Primary Examiner—Alfred E. Smith
Assistant Examiner—Carolyn E. Fields
Attorney, Agent, or Firm—Diller, Ramik & Wight

[57] ABSTRACT

The invention relates to a method of checking the coating of a metal surface, in which the surface to be checked is exposed to electro-magnetic radiation and the amount of reflected radiation is measured and compared with the amount incident to the surface exposed.

The invention also relates to a device for carrying out such method.

3 Claims, 3 Drawing Figures

METHOD OF CHECKING THE COATING OF A METAL SURFACE AND DEVICE FOR CARRYING OUT THE SAME

The invention relates to a method of checking the coating of a metal surface.

A method of checking the coating of metal containers and a device for carrying out the same are known. In the technology hitherto known the inner wall of said metal containers has been provided with a double coating. The purpose of such a double coating is to provide the certainty of a complete coating of the surface. However, the use of a double coating instead of a single one has the disadvantage that the second coating has to be applied in a separate run, which involves an increase in costs, whilst in addition more material has to be used for the coating. It is, therefore, obvious that the use of a single coating rather than a double one can bring about considerable saving. On the other hand, however, when applying a single coating defects or disturbances of the device employed for applying the coating may result in impermissible deterioration of the product.

With regard to the foregoing, in checking the coating of metal containers, it is not sufficient, in contrast to what has hitherto been common practice, to carry out random checks, on the contrary all containers have to be checked after the application of the coating.

In connection with the above the invention has for its object to provide a method and a device by which, in general in a highly reliable manner and in particular at a high rate, all metal objects successively emanating from a production line can be checked with regard to the properties of a coating applied thereto.

To this end the invention proposes a method of the kind set forth in the preamble, in which the surface to be checked is exposed to electro-magnetic radiation and the amount of reflected radiation is measured and compared with the amount incident to the surface exposed. Preferably the method embodying the invention is characterized in that two monitoring members are employed, one of which receives radiation directly and the other via the surface to be checked and in that the output signals of the monitoring members are compared with one another.

Very satisfactory results are obtained when the surface to be checked is exposed to radiation which the coating is capable of absorbing to an appreciable extent.

According to the invention it is preferred to use a method in which the coating is formed by a transparent lacquer and the wavelength spectrum of the electromagnetic radiation mainly extends solely below 350 nm.

A device for carrying out the method embodying the invention may be characterized by a source of radiation, a monitoring member for measuring the radiation reflected by the surface to be checked and means for comparing the output signal of said monitoring member with a second signal representative of the amount of radiation incident to the surface. There may be provided, for example, a second monitoring member for measuring the amount of radiation dispensed by the radiation source and the dispension of said second signal.

A preferred embodiment of the device in accordance with the invention comprises transport means for successively passing the objects having a surface to be checked along the radiation source and an ejecting member coupled for control with the comparing means.

In order to ensure the finest possible discrimination the device embodying the invention may comprise a filter arranged between the radiation source and the surface to be checked, said filter, whilst passing the wave range to be used, suppressing to a considerable extent further wavelengths of the radiation emitted by the source and any interfering radiation. In this way optimum adaptability of the wavelength(s) used to the absorptive properties of the coating is ensured.

The radiation source may comprise at least one and preferably three gas discharge tubes connected each to a different phase of a threephase mains. Such a three-phase circuitry provides an excellent uniformity of the emitted radiation, whilst nevertheless all three gas discharge tubes are fed by alternating current, which is highly conducive to the lifetime.

The or each gas discharge tube may be filled, for example, with hydrogen, xenon or mercury vapour. In the latter case the aforesaid filter may be designed to suppress wavelengths exceeding 253.7 nm. In such a configuration it is ensured that the important mercury line of 253.7 nm, for which particularly transparent lacquer exhibits a high absorptive power, can operate most effectively without the risk of erroneous fault indications due to the presence of spectral components for which the lacquer has less high an absorptive power.

In the case mentioned above in which two monitoring members are used i.e. one for measuring the radiation reflected by the surface to be checked and one for measuring the amount of radiation incident to said surface, the two monitoring members are preferably thermally coupled. In this way a satisfactory constance of an approval/disapproval criterion is ensured even for a long time. For the thermal coupling there may be used a copper plate on both sides of which the monitoring members are arranged.

Preferably the position of at least the first monitoring member is adjustable, since balancing between the sensitivity to radiation emanating, for example, from the bottom of the metal container and the radiation emanating from the cylindrical wall of the container may thus be obtained.

Figure 4:
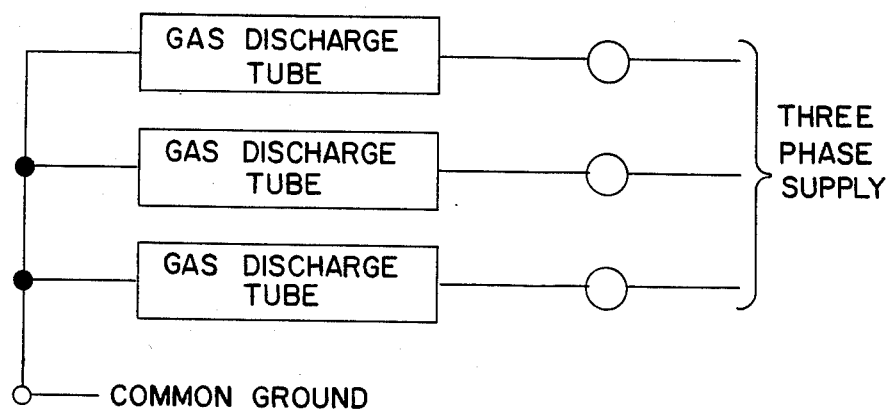
Figure 5:
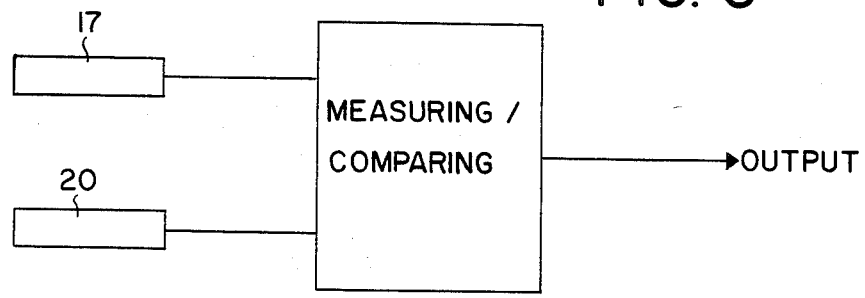

The invention will now be described more fully with reference to a drawing which shows inter alia a random embodiment for checking the internal coating of a metal container. The drawing shows in FIG. 1 a fragmentary perspective view of a device embodying the invention, FIG. 2 a cross-sectional view of a detail of the device embodying the invention, FIG. 3 a graph in which the reflection coefficient of a transparent lacquer layer and that of an untreated metal are plotted against the wavelength of the radiation employed, FIG. 4 is a view illustrating the electrical supply to the gas tubes, and FIG. 5 is a diagrammatic view of the connection of the two monitors to the measuring/comparing means.

FIG. 1 shows a transport device 1 for tinned-iron containers, one of which is designated by reference numeral 2. The transport device 1 comprises a conveyor belt 3, a magnetic strip 4 and guide strips 5, 6. The transport direction is indicated by an arrow 7.

The housing 8 comprises below a reflector 9 three tubular mercury vapour lamps 10, 11, 12 producing grosso modo a radiation in the direction indicated by the arrows 13.

A portion of the radiation emitted by the lamps 10, 11, 12 is incident through a quartz window 14 to the interior of the container 2. The radiation reflected from the interior of the container 2 indicated by the arrows 25 is incident through the quartz window 14 and a first bandpass filter 15 to a first monitoring member 17 arranged on a copper plate 16.

A further portion of the radiation passes through an aperture adjusting plate 18 and a second bandpass filter 19 and then strikes a second monitoring member 20 arranged on the other side of the copper plate 16.

The mercury vapour lamps 10, 11, 12 emit a radiation having a line spectrum in which by a correct choice of the pressure of the mercury vapour the line of a wavelength 253.7 nm is very strongly represented. The bandpass filters 15 and 19 are designed for suppressing spectral components of larger wavelength.

The aperture adjusting plate 18 serves for optimally balancing the "reference value" corresponding to the output signal of the second monitoring member 20 and the output signal of the first monitoring member 17 for the case in which an untreated tin is checked.

Figure 2:
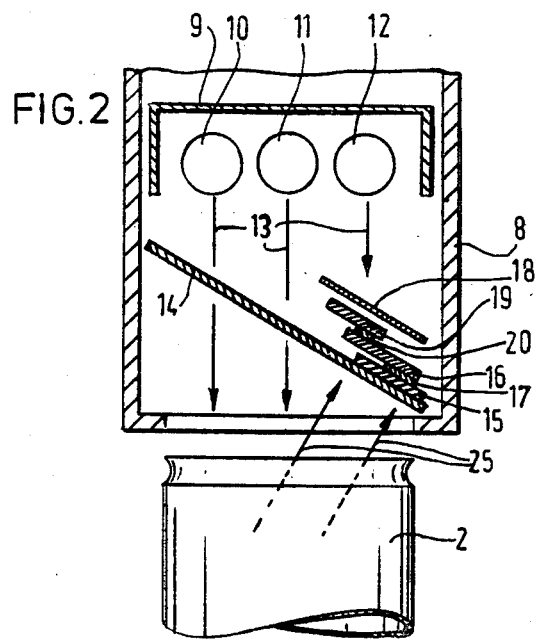

It should be noted that in FIG. 2 the last-mentioned details of the arrangement are more clearly apparent than in FIG. 1.

For checking the presence and the correct position of a container 2 to be checked two detection members 26, 27 are provided. The detection member 26 is located, as shown viewed in the transport direction 7, in front of and on a higher level than the detection member 27. Owing to the difference in height between the members 26 and 27 it is possible to detect any container toppled over. By the displacement in the longitudinal direction the speed of the passing container 2 can be assessed. By means not shown and on the basis of these data an expeller 28 shown schematically can be actuated at the correct instant for conducting away a disapproved container, by the displacement of a plunger 30 in the direction of the arrow 29, through an opening 31 in a sidewall 32 via a gutter 33 in the direction indicated by the arrow 34.

Not only by the signals from the detection members 26 and 27 but also on the basis of the signals emanating from the monitoring members 17 and 20 being indicative of the presence of the coating the expeller 28 is actuated. Said two monitoring members are coupled with means for comparing the output signals of the two members. If it is found by the comparison by the means (not shown) that the output signal of the first monitoring member 17 has too high a value which corresponds to an inadequate coating of the container 2, the expeller 28 receives an energizing signal after a period of time determined by the longitudinal distance between the detection members 26 and 27 so that the disapproved container is expelled through the gutter 33.

Approved containers pass by a third detection member 35, which may serve to count the number of approved containers.

It is noted that the conveyor belt 3 is guided in a channel 36 of a block 37. The housing 8 as well as the detection members 26, 27, 35, the expeller 28 and the guide strips 5 and 6 are fastened to a rear wall 38.

Figure 3:
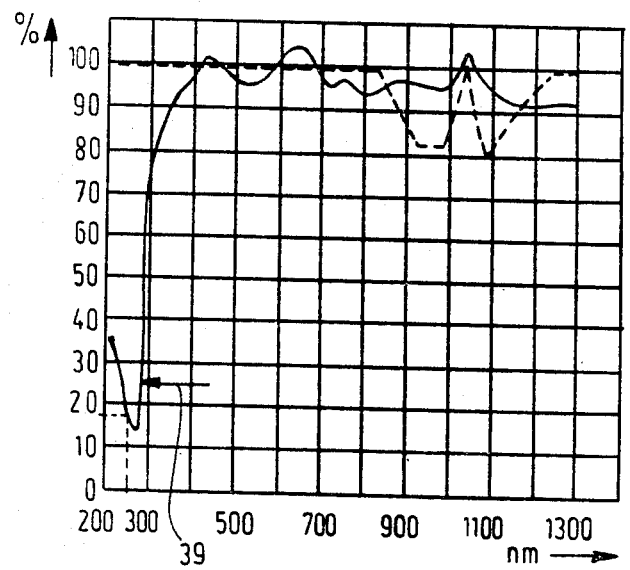

FIG. 3 shows by a solid curve the reflection coefficient expressed in a percentage of a transparent lacquer as a function of the wavelength of the incident radiation. The broken curve indicates the reflection coefficient of an untreated surface. From the solid curve it is clearly apparent that the absorption for wavelengths below 350 nm has a considerable value: the reflection coefficient is appreciably lower than 100%. From the graph it is evident that in the ideal case a wavelength of about 270 nm should be used. Mercury vapour discharge tubes emit a radiation having a line of 253.7 nm. The graph shows that for this wavelength the reflection coefficient is also very low, that is to say, about 17%. For this reason it is preferred to use mercury vapour lamps in which the mercury vapour pressure is chosen so that said spectral line has an optimum relative intensity. Such lamps are commercially available as germicide lamps.

FIG. 3 indicates by way of example by an arrow 39 a threshold value, at the transgression of which a fault is announced to the expeller 28. The threshold value is chosen here to be about 25%.

It should be noted that in the wavelength range below 350 nm the reflection of untreated metal surfaces is substantially 100%.

It will be obvious that the mode of processing the signals from the monitoring members and the detection members may be chosen at will. It may be imagined, for example, to use a micro-computer. In the latter case the memory space of the micro-computer may be used for collecting the data of one day, a production series or the like, whilst moreover a classification of reflection levels may be made, on the basis of which for example, the threshold value 39 can be adapted.

It is furthermore noted that other transport means than those shown in FIG. 1 may be employed. If aluminium tins are used a sufficiently rough conveyor belt may be used, whilst the tins are held in place by gravity.

Obviously, many variants are lying within the scope of the invention.

We claim:

1. Apparatus for checking the presence of discontinuities in the coating of a metal surface, which comprises emitting means for emitting electro-magnetic radiation onto the coated surface whose wavelength spectrum includes wavelengths for which the coating is highly absorptive as well as wavelengths for which the coating is only slightly absorptive, first monitoring means for receiving electro-magnetic radiation reflected from said coated metal surface and for producing an output signal whose value increases as the intensity of reflected radiation impinging thereon increases, first filter means for allowing substantially only that reflected radiation which corresponds to the wavelengths for which the coating is highly absorptive to impinge upon said first monitoring means, second monitoring means for receiving electro-magnetic radiation emitted by said emitting means and for producing an output signal whose value increases as the intensity of radiation impinging thereon increases, and second filter means for allowing substantially only radiation emitted by the emitter means which corresponds to the wavelengths for which the coating is highly absorptive to impinge upon said second monitoring means, whereby the difference between the values of said output signals indicates the presence of discontinuities of said coating, and a radiation-opaque mounting plate having one face directed toward said coated surface and an opposite face directed toward said emitting means, said first monitoring means being mounted on said one face and said second monitoring means being mounted on said opposite face.

2. Apparatus as defined in claim 1 wherein said mounting plate is made of metal having high thermal conductivity whereby said first and second monitoring means are thermally coupled.

3. Apparatus as defined in claim 2 including aperture window means for adjusting the intensity of radiation impinging upon said second monitoring means through said second filter means to establish a reference value corresponding to the output of the second monitoring means and the output signal of said first monitoring means for the case in which an uncoated metal surface is being checked.

* * * * *